United States Patent
Berggren et al.

(10) Patent No.: US 7,531,128 B2
(45) Date of Patent: May 12, 2009

(54) ARRANGEMENT, DEVICE, METHOD, PRODUCT AND USE IN CONNECTION WITH A BLANK MADE PREFERABLY OF TITANIUM POWDER AND INTENDED FOR A DENTAL CROWN OR OTHER PRODUCT FOR THE HUMAN BODY

(75) Inventors: Carina Berggren, Torslanda (SE); Mikael Eriksson, Mölndal (SE)

(73) Assignee: Nobel Biocare AB, Göteborg (SE)

( * ) Notice: Subject to any disclaimer, the term of this patent is extended or adjusted under 35 U.S.C. 154(b) by 644 days.

(21) Appl. No.: 10/500,030

(22) PCT Filed: Dec. 19, 2002

(86) PCT No.: PCT/SE02/02386

§ 371 (c)(1),
(2), (4) Date: Jun. 24, 2004

(87) PCT Pub. No.: WO03/061509

PCT Pub. Date: Jul. 31, 2003

(65) Prior Publication Data
US 2005/0126337 A1    Jun. 16, 2005

(30) Foreign Application Priority Data
Dec. 28, 2001    (SE) .................................... 0104445

(51) Int. Cl.
*B22F 3/00*    (2006.01)
*B28B 3/00*    (2006.01)

(52) U.S. Cl. .......................... 419/38; 264/632; 264/635

(58) Field of Classification Search ................... 419/38; 425/78
See application file for complete search history.

(56) References Cited

U.S. PATENT DOCUMENTS

| 3,852,045 A | * | 12/1974 | Wheeler et al. | .............. 428/566 |
| 4,431,449 A | * | 2/1984 | Dillon et al. | .................. 75/246 |
| 2003/0167938 A1 | * | 9/2003 | Olsson | .................. 100/269.01 |

FOREIGN PATENT DOCUMENTS

| WO | WO-0015137 A1 | 3/2000 |
| WO | WO-0030788 A1 | 6/2000 |

* cited by examiner

*Primary Examiner*—Roy King
*Assistant Examiner*—Ngoclan T Mai
(74) *Attorney, Agent, or Firm*—Connolly Bove Lodge & Hutz LLP

(57) ABSTRACT

An arrangement for producing a blank made of metal powder, preferably titanium powder, intended for a dental crown or other product for the human body (spacer, dentine, implant, etc.) comprises at least one first apparatus for powder compression and at least one second apparatus with one or more elastic molds having at least one cavity for a punch (block) and the powder used in the initial stage. The first apparatus comprises a machine operating by impact compaction, and said mold or molds is/are arranged, when the cavity is filled with starting powder, to receive impacts effected by the impaction members in the machine and, as a function of the impact or impacts, to generate an isostatic action during the compression/compaction. The invention also relates to a device, method and use and permits a rapid production procedure while maintaining the current requirements in respect of precision and quality.

13 Claims, 3 Drawing Sheets

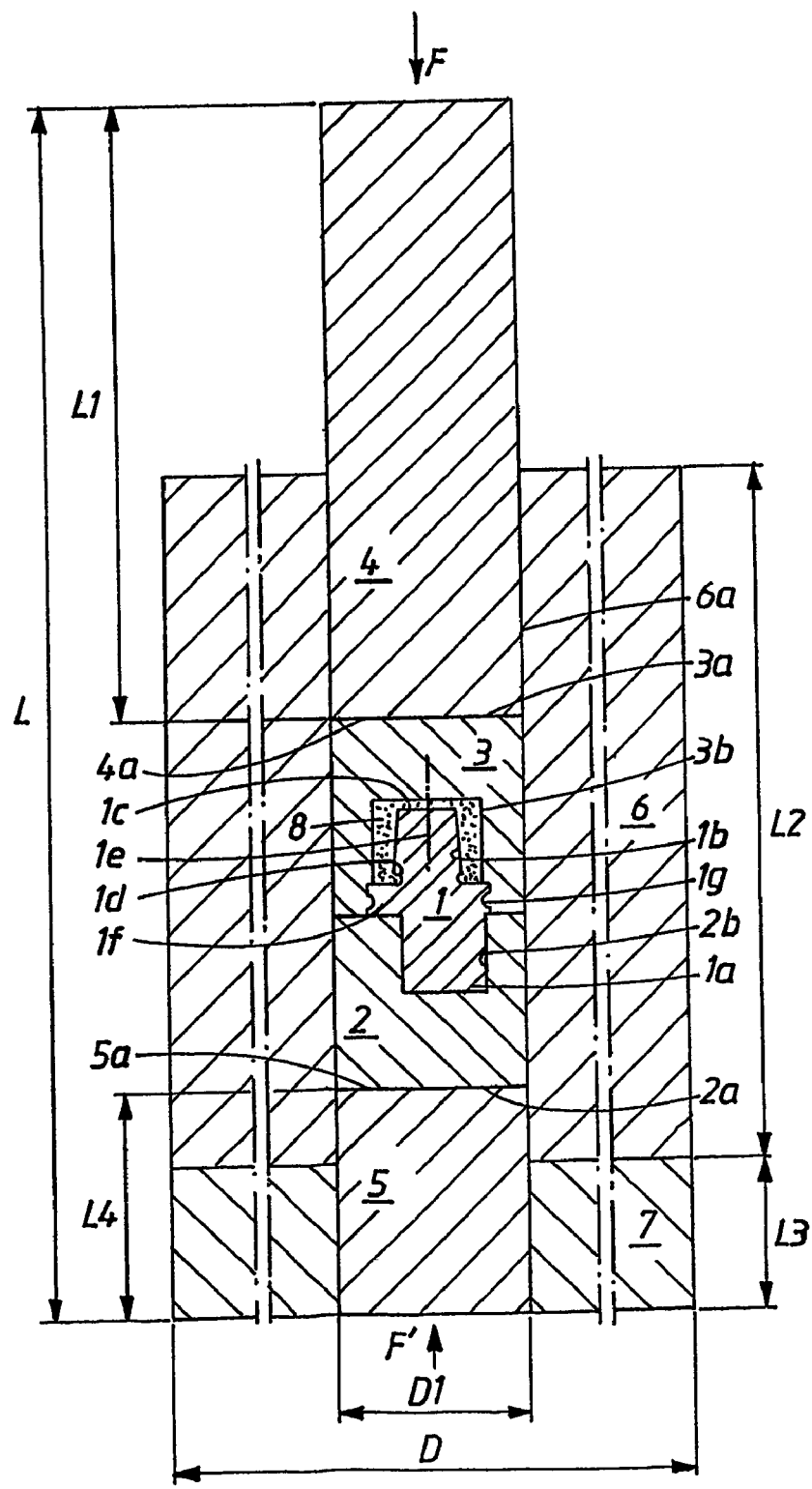

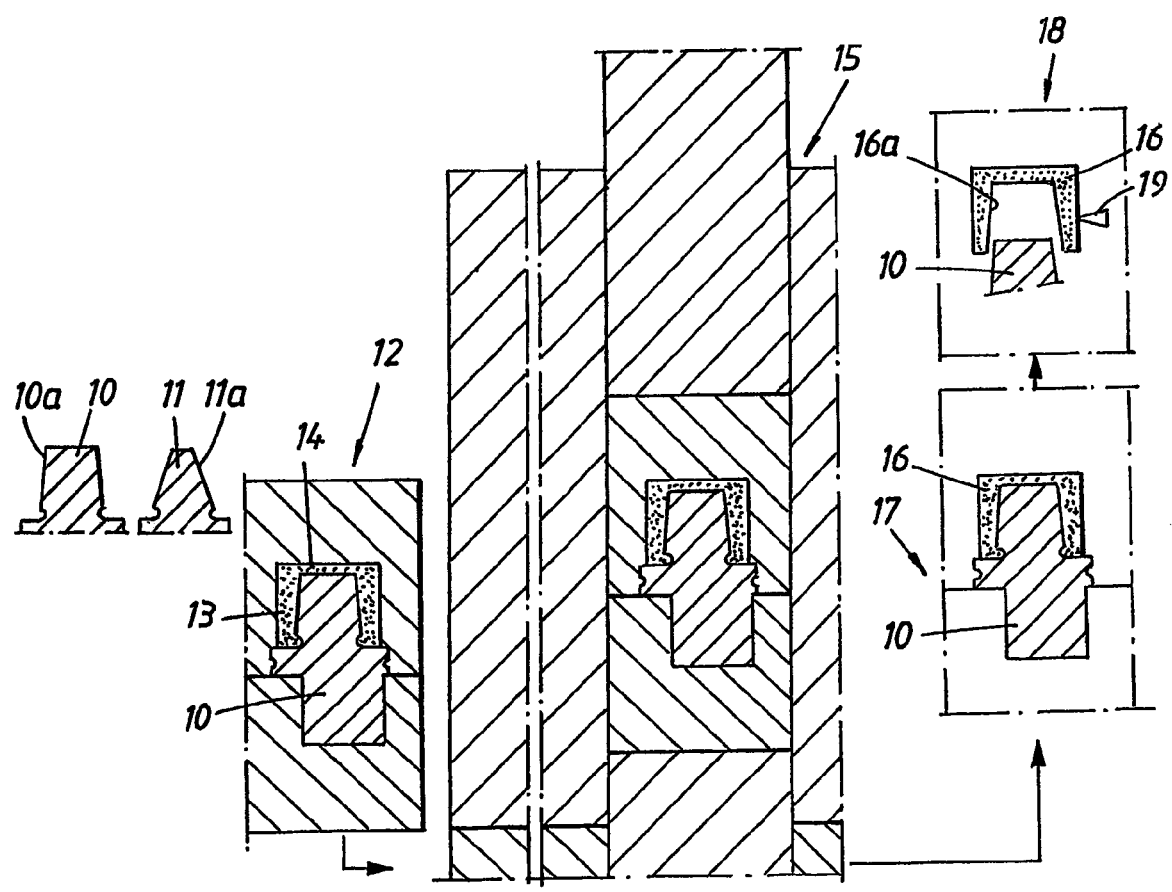

ARRANGEMENT, DEVICE, METHOD, PRODUCT AND USE IN CONNECTION WITH A BLANK PREFERABLY OF TITANIUM POWDER AND INTENDED FOR A DENTAL CROWN OR OTHER PRODUCT FOR THE HUMAN BODY

The present invention relates inter alia to an arrangement for producing a blank made of powder, preferably titanium powder, intended for a dental crown or other product for the human body, which can be a spacer, dental bridge, implant, etc. The arrangement comprises at least one first apparatus for powder compression and at least one second apparatus with one or more elastic molds having at least one cavity for a punch or block and the powder which is used in the initial stage. Said powder is referred to here as starting powder. The invention also relates to a device for considerably reducing or eliminating the need for sintering of a blank comprising or consisting of powder material and intended for a dental crown or other product for the human body. In addition, the invention relates to a method, a product and a use of the blank for a dental crown or other product for the human body comprising or consisting of compressed or compacted material powder, which can be titanium powder, or a powder of gold alloy, steel, etc.

The present invention can be seen as a development of the invention according to PCT WO 00/15137 from the same Applicant. The invention is based inter alia on production of a blank for dental crowns, dental bridges, spacers, implants, etc. The products in question often have very thin walls (400-600 μm) and must have individual shapes and be able to be designed with great precision (e.g. 0.2 μm). See, inter alia, said PCT specification.

In connection with the present invention, use is made of a machine referred to as an impact-type compaction machine which operates with high-velocity compaction and can provide impacts with a high energy content per unit of time, for example an energy content of up to 4500 Newton meters. Such a machine is available on the market from Hydropulsor, Sweden, under the reference HYP35-18.

In connection with the production of said dental crowns and products, there is a need to be able to rationalize the production and shorten the production times while maintaining the existing production accuracies. The main object of the present invention is to solve this problem among others. In addition, there may be a desire to improve the product in question from the point of view of its strength. In accordance with the concept of the invention, the above is achieved by tighter compression of the powder material, which in turn can substantially reduce and simplify the sintering. Shrinkage can be reduced and better geometric stability can be achieved. In the present case, a harder initial compression of the powder particles is achieved with the aid of impact compaction. However, existing arrangements, methods and devices cannot be used without important measures in accordance with the invention having to be taken. Thus, for example, the known machine for high-velocity compaction cannot be used directly since it has hitherto been considered to operate with only two-dimensional energy transfer to the product which is to be produced. In the case of three-dimensional bodies in accordance with the present invention, there must be an isostatic pressing function or an isostatic pressing action for the bodies. It is an object of the present invention to permit the use of a two-dimensional transfer to give a three-dimensional effect on the powder material in the mold so that the compression is homogeneous in all parts of the product. The energy must therefore be able to be obtained and distributed about the whole of the three-dimensional product and not just applied straight from above, the aim of this being to spread the compression around the whole punch and ensure that the compaction is uniform.

There is also a requirement to be able to operate with a continuous sintering function. The previously used vacuum method with sintering times of 6-7 hours means that a large number of compressed and as yet unsintered products must be gathered together in a common sintering step. It has been difficult to separate defective samples manually. The invention solves this problem too with the aid of substantially reduced sintering times in the oven or sintering only in protective gases.

The feature which can principally be regarded as characterizing an arrangement according to the invention is that the first apparatus mentioned at the outset comprises a machine operating by impact compaction, and that said mold or molds is/are arranged, when the cavity is filled with starting powder, to receive one or more impacts effected by the impaction members in the machine and, as a function of the impact or impacts, to generate an isostatic action during the effected compression/compaction.

In further developments of the inventive concept, the mold comprises top and bottom molds which can be applied in a recess in a die. The top and bottom molds can be arranged with a first space for insertion or positioning of the punch. At least one mold of the top and bottom molds has a second space for the powder, and the top and bottom molds can also be arranged to cooperate in said recess in the die with upper and lower stamps or with a stamp and a support at their end surfaces. Upon activation of the stamps against one another, or upon activation of the stamp against the support, there is a substantially uniform pressing of the powder against the whole outer surface of the stamp. Further developments of the invention will emerge inter alia from the dependent claim concerning the arrangement in question.

The feature which can principally be regarded as characterizing a device for substantially reducing or eliminating the need for sintering is that, by means of impact compaction with a high energy per unit of time, the blank acquires and has a substantial density, namely densities of at least ca. 98% or higher.

A method of the invention is characterized inter alia by production or selection of a punch or block with an outer shape corresponding to the inner shape of the blank. In subsequent steps, the punch and the starting powder are applied in the inner space in a mold consisting of an elastic material, and the mold with the punch and the starting powder is applied in an impact-type compaction machine. In this, high energy per unit of time is transferred to the mold in the machine, and the transmitted energy is distributed by means of an isostatic function or isostatic action which is obtained by means of the design and arrangement of the mold and the punch. Finally, the novel method is characterized by sintering of the compressed powder for a relatively short time, preferably a time of 30 minutes to 2 hours, in a sintering unit operating with or without a vacuum function.

A product according to the invention is characterized mainly in that the blank in question has a high density, for example a density (theoretical density) of 90% or higher. The density is preferably chosen in the range of 95-99.5%.

A use according to the invention is characterized in that an impact-type compaction machine effecting a high energy per unit of time is used for compressing or compacting the powder in connection with the production of the blank in question for a dental crown or other product for the human body.

By means of what has been proposed above, suitable dental crowns or similar can be produced with the aid of impact energies which can be 1200 Nm or higher. Different numbers of impacts can be used in the production of symmetrical dental crowns made of titanium. Thus, for example, 1, 2, etc., impacts can be used, it being possible to vary the impact energy. By means of the invention, it is possible to produce well compacted products in a rapid and potentially less expensive way than has hitherto been possible. Earlier genetically used bodies, for example dental crowns, can be produced using titanium material used earlier in this connection, see the PCT application mentioned in the introduction. In connection with the impact-type compaction machine, it is possible to use means which promote movement or sliding, for example vaseline, Castrol APS2, etc., in the space in which the rubber mold and the stamps work. Tests have shown that dental crowns of a given type can be produced as homogeneous bodies with 1500 Nm×1 impact. The desired compression of the titanium body was achieved around the surface of the whole punch.

The invention will be described below on the basis of an arrangement, a device, a method, a product and a use, with reference to the attached drawings in which FIG. 1 shows, in vertical section, parts of a partially known impact-type compaction machine provided with a mold comprising punch and powder for a blank for a dental crown, FIG. 2 shows, in vertical section, a concrete embodiment of a blank for a dental crown made of compacted titanium powder together with parts of a spacer, use having been made of an energy level of 1500 Nm and three impacts, FIG. 3 shows, in vertical section, a second embodiment of a corresponding blank and punch, where a movement energy of 1800 Nm has been used in combination with two impacts, FIG. 4 shows, in a vertical view, a third embodiment of a corresponding dental crown and punch, where an energy of 1500 Nm has been used together with one impact, and FIG. 5 shows, in a vertical and diagrammatic view, the production of a machine-workable blank for a dental crown.

In FIG. 1, a punch or block which determines the inner geometry of the dental crown is indicated by 1. The punch can be made of aluminum AA 6262. Data on such a material is known per se and will therefore not be described here. FIG. 1 also shows a bottom mold or a first mold indicated by 2. The mold is made of silicone designated by DG-A-Sil (DUBLI-SIL 15) which, as is known, is a material used in dentistry. Data on such a material is also already well known and will not be described here. A top mold or second mold which can cooperate with the bottom mold or the first mold is indicated by 3. The second mold has the same material as the first mold. An upper stamp included in the machine is indicated by 4 and is made of V30, Uddeholm. A lower stamp 5 is made of the same material as the upper stamp. The second mold 2 is designed such that its end surface 2a can cooperate with a top surface 5a of the lower stamp. Correspondingly, the top mold 3 cooperates via a top surface 3a with a lower end surface 4a of the upper stamp. The machine also comprises a die 6 consisting of a hard metal insert made of WC/cobalt alloy with shrunk-on ring. Reference number 7 indicates a spacer ring which can be regarded as part of the machine's base plate. The die is provided with a recess 6a in which the molds 2 and 3 and the stamps 4 and 5 are arranged. To guarantee the required sliding function in the recess 6a, a slide-promoting agent of a type known per se (see above) can be used in connection with the molds and stamps. The stamps can be movable toward and away from one another and, upon application of the mold with the punch and powder in it, the stamp 4 for example can be removed completely from the recess 6a and the mold 2, 3 can be applied. In FIG. 1, forces F, F' have been indicated, by means of which the energy from the stamps is transmitted to the mold 2, 3 and the punch 1 lying therein. Upon compaction, the elastic material of the top and bottom molds is forced against the punch, with the powder lying between them. The bottom mold 2 is provided with a recess 2b in which the lower parts 1a of the punch are placed. Correspondingly, the top mold is provided with a recess 3b. A mold cavity 8 is obtained between the wall of the recess 3b and the outer surfaces 1b of the punch and a top surface 1c. The punch is provided with a narrowing or waist shape 1d, and the top part of the punch whose outer surfaces 1b and 1c form the inner space of the dental crown merge with the lower parts 1a of the punch via a flange 1f. The flange too is provided with a narrowing 1g at its middle parts. The outer surface 1b of the punch is slightly cone-shaped in order to permit a subsequent release function between the punch and the blank formed by powder. Tests have shown that the illustrated design allows the mold and the punch to operate with an isostatic action in which the powder is pressed by the energy transmitted from the stamps 4, 5 or the machine in a uniform manner around the whole punch. In one illustrative embodiment, the rubber molds have a diameter of ca. 25 mm and a total height of ca. 50 mm. The punch has a height of ca. 25 mm or a height which is about half the height of the rubber molds. The bearing part of the punch in the respective mold recess has a height of ca. 10 mm and a diameter of ca. 10 mm. The height of the flange is 2-3 mm and the diameter of the flange is ca. 15 mm. The flange can also be considered to be slightly offset in the transverse plane relative to the bearing part. The top part of the punch which supports that surface of the blank determining the inner shape has a height, diameter or other relevant dimension which is a function of the height and wall thickness of the blank. The mold cavity for the powder is also chosen as a function of the configuration of the blank. The walls of the rubber molds around the punch and the mold cavity are also chosen as a function of the impact energy of the machine, the number of impacts, etc. The wall thicknesses above and below the punch exceed the wall thicknesses at the side of the punch.

The impact energy from the stamps must exceed 900 Nm and is preferably chosen in the range of 1200-1800 Nm. The molds must have a high degree of softness and are made for example with a Shore number in the range of 10-40, preferably in the range of 15-20. The result of the energy transfer is that the compacted blank can be given a high density (theoretical density). This density will preferably exceed ca. 95%. The titanium powder which in the present case has a weight of ca. 3 g consists of Wah Chang HP (or CP)—325 Nech. In FIG. 1, the lengths of the different parts have been indicated by L, which can be ca. 160 mm, L1 which can be 80 mm, L2 which can be 90 mm, L3 which can be 20 mm, and L4 which can be 30 mm. The external diameters D of the parts 6 and 7 are ca. 200 and the diameters D1 of the stamps are ca. 25. The mold 2, 3 and the stamps 4 and 5 can have circular cross sections. As regards the particle sizes of the powder, the densities, etc., reference is also made to the above and to said PCT application.

In FIG. 2, the blank made of compressed powder has been indicated by 9. The upper parts 1e of the punch have also been shown in FIG. 2. Said punch parts can be polish-etched. The figure derives from a test which was carried out in which an energy of 1500 Nm was used. The number of impacts in this case was three.

FIG. 4 shows a third illustrative embodiment with the blank 9" and the punch part 1e", where an energy of 1500 Nm with one impact was used. It should be noted here that all the powder material in the blank does not need to be compacted maximally in cases where some portions are not expected to be included in the final mold for the dental crown or similar.

Figure 2:
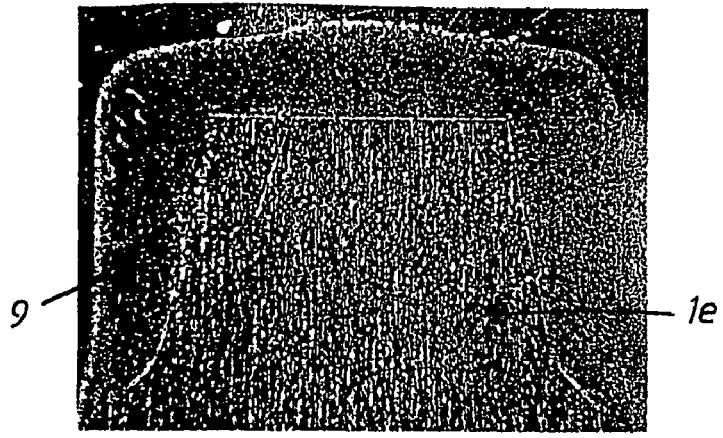
Figure 3:
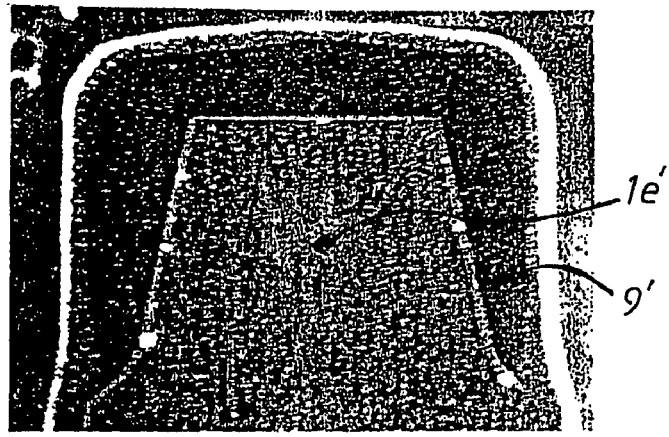
FIG. 3 shows a case in which the body or the blank 9' has been pressed against the punch part 1e' with an energy of 1800 Nm, where the pressing or impacting procedure was carried out with two impacts.
Figure 4:
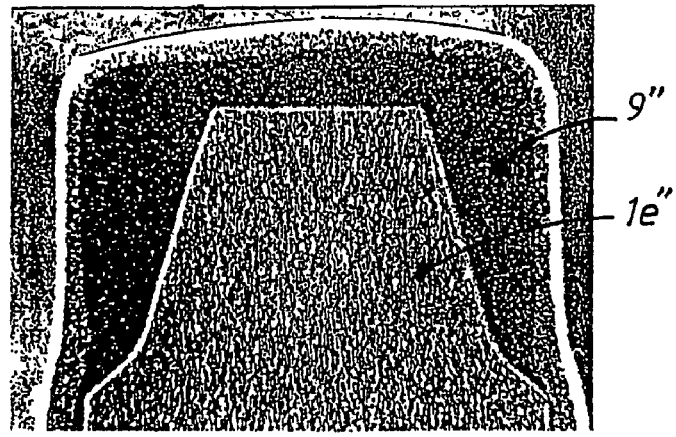

In the cases according to FIGS. 2, 3 and 4, a blank can be obtained with a substantial density of the used powder, preferably a density of ca. 98% of higher.

FIG. 5 is intended to show a method in which a blank for a dental crown is produced. In a first step, a punch or block 10 or 11 is produced or selected with an outer shape 10a, 11a, respectively, which relates to the inner shape of the blank. The selected punch is applied in the mold which is made of the elastic material mentioned above. In the present case, the spacer 10 is assumed to have been selected and placed in the mold 12. A powder material, preferably of titanium 13, has been placed in the mold cavity which has been indicated by 14. The mold 12 with the punch and the powder is applied in the impact-type compaction machine 15 and, after the compaction, the compressed material or the blank 16 is transferred to a sintering unit 17. The blank is at this stage attached to the punch 10. In a demolding and machining step 18, the blank 16 can be separated from the punch 10. The demolding can be done in a manner known per se, for example by selection of different coefficients of expansion of the blank and the punch, see also said PCT application. The blank 16 can be given its final outer shape by machining, which has been shown diagrammatically by 19. Said machining can be done using various recognized methods, for example by turning, milling, etc., see said PCT application. The inner space 16a corresponds to the outer surface 10a of the punch.

The use of a blank of the type in question can thus be regarded as being characterized by the fact that an impact-type compaction machine which develops great energy is used for compressing or compacting the powder 13.

The invention is not limited to the configuration described above as an illustrative embodiment, and instead it can be modified within the scope of the attached patent claims and the inventive concept.

The invention claimed is:

1. A method for producing a blank made of powder and intended for a product for the human body,
   a) producing or selecting a punch with an outer shape corresponding to the inner shape of the blank,
   b) applying the punch and a starting powder in an inner space of a mold of elastic material,
   c) applying the mold with the punch and the starting powder in an impact-type compaction machine,
   d) transferring high energy per unit of time from at least one impaction member of the impact-type compaction machine to the mold in the machine,
   e) distributing the transferred energy by means of an isostatic function which is generated by means of the mold to compress the starting powder, and
   f) sintering the compressed powder, wherein the mold applied to the impact-type compaction machine comprises a top portion and a bottom portion configured to be assembled together and applied to a recess in a die.

2. The method of claim 1, further comprising:
applying a slide-promoting agent in the recess for the top portion and bottom portion.

3. The method of claim 1, further comprising:
machining the compressed powder prior to use in a product for the human body, wherein the product for the human body is a dental crown.

4. The method of claim 1, wherein said transferring high energy per unit of time to the mold in the machine comprises delivering at least one impact upon the mold with the at least one impaction member of the machine.

5. The method of claim 4, wherein the at least one impaction member delivers a high impaction energy in excess of 900 Nm (Newton meters) to the mold upon said delivering at least one impact.

6. The method of claim 1, wherein the mold in which the punch and the starting powder are applied is configured to have a degree of softness defined by a Shore number in the range of 10-40.

7. The method of claim 1, wherein the mold in which the punch and the starting powder are applied comprises silicone.

8. The method of claim 1, wherein said distributing said transferred energy to compress the staffing powder is configured to provide a compressed starting powder density of 90% or higher.

9. The method of claim 1, wherein said distributing said transferred energy to compress the staffing powder is configured to provide a compressed starting powder density of 95%-99.5%.

10. The method of claim 1, wherein the staffing powder applied in the inner space comprises one of at least Wah Chang HP -325 Mesh and Wah Chang CP -325 Mesh.

11. The method of claim 1, wherein said sintering is performed in a sintering unit for a duration of 30 minutes to 2 hours, operating with or without a vacuum function.

12. The method of claim 1, wherein the product for the human body is a dental crown.

13. The method of claim 1, wherein the punch has a narrowed or waist-shaped portion.

* * * * *